United States Patent
Verbeek et al.

(10) Patent No.: US 7,079,895 B2
(45) Date of Patent: Jul. 18, 2006

(54) CARDIAC PACING FOR OPTIMAL INTRA-LEFT VENTRICULAR RESYNCHRONIZATION

(75) Inventors: Alexander Adrianus Martinus Verbeek, Roermond (NL); Frits W. Prinzen, Maastricht (NL)

(73) Assignee: Medtronic, Inc., Minneapolis, MN (US)

(*) Notice: Subject to any disclaimer, the term of this patent is extended or adjusted under 35 U.S.C. 154(b) by 531 days.

(21) Appl. No.: 10/424,192

(22) Filed: Apr. 25, 2003

(65) Prior Publication Data

US 2004/0215252 A1 Oct. 28, 2004

(51) Int. Cl.
A61N 1/36 (2006.01)
(52) U.S. Cl. .......................................... 607/9
(58) Field of Classification Search ................ 607/9, 607/15
See application file for complete search history.

(56) References Cited

U.S. PATENT DOCUMENTS

| | | | |
|---|---|---|---|
| 5,024,222 A | | 6/1991 | Thacker |
| 5,129,393 A | * | 7/1992 | Brumwell ........................ 607/9 |
| 5,179,949 A | * | 1/1993 | Chirife ............................ 607/9 |
| 5,330,511 A | | 7/1994 | Boute |
| 5,334,222 A | | 8/1994 | Salo et al. |
| 5,507,782 A | * | 4/1996 | Kieval et al. .................... 607/9 |
| 5,540,727 A | | 7/1996 | Tockman et al. |
| 5,584,868 A | | 12/1996 | Salo et al. |
| 5,626,623 A | | 5/1997 | Kieval et al. |
| 6,070,100 A | * | 5/2000 | Bakels et al. .................... 607/9 |
| 6,144,880 A | | 11/2000 | Ding et al. |
| 6,223,079 B1 | * | 4/2001 | Bakels et al. .................... 607/9 |
| 6,285,907 B1 | * | 9/2001 | Kramer et al. .................. 607/9 |
| 6,449,510 B1 | | 9/2002 | Albers et al. |
| 2001/0016759 A1 | * | 8/2001 | Kramer et al. .................. 607/9 |
| 2002/0133198 A1 | | 9/2002 | Kramer et al. .................. 607/9 |

FOREIGN PATENT DOCUMENTS

WO  WO 99/30777  6/1999

OTHER PUBLICATIONS

Auricchio et al., "Cardiac Resynchronization Therapy Restores Optimal Atrioventricular Mechanical Timing in Heart Failure Patients with Ventricular Conduction Delay" *J. Am Coll Cardiol 2002*; 39:1163-9.

Grosfeld et al., "Testing a New Mechanism for Left Ventricular Septal Spacing: The Transseptal Route", *Europace*; vol. 4, Oct. 2002: 439-444.

(Continued)

*Primary Examiner*—Robert E. Pezzuto
*Assistant Examiner*—Yun H. Lee
(74) *Attorney, Agent, or Firm*—Paul H. McDowall; Girma Wolde-Michael (57) ABSTRACT

Cardiac pacing to treat ventricle dysynchrony for improved cardiac function is performed as follows. Early paced inter-ventricular asynchrony is determined during ventricular pacing. Baseline inter-ventricular asynchrony is determined without pacing. Average inter-ventricular asynchrony is calculated by averaging the early paced inter-ventricular asynchrony and the baseline inter-ventricular asynchrony. Atrioventricular delay and ventricular-ventricular delay are adjusted during ventricular pacing to yield the average inter-ventricular asynchrony for optimal intra-left ventricular resynchronization and maximal cardiac function. The elements above can be configured in software contained in an implantable medical device or embodied as a computer software product that includes a medium readable by a processor.

15 Claims, 12 Drawing Sheets

OTHER PUBLICATIONS

Kass et al. "Improved Left Ventricular Mechanics from Acute VDD Pacing in Patients with Dilated Cardiomyopathy and Ventricular Conduction Delay" *Circulation 1999*; 99(12):1567-73.

Peschar et al., "Left Ventricular Septal and Apex Pacing for Optimal Pump Function in Canine Hearts", *Journal of the American College of Cardiology*; 41(7), 2003:1218-1226.

* cited by examiner

CARDIAC PACING FOR OPTIMAL INTRA-LEFT VENTRICULAR RESYNCHRONIZATION

FIELD OF THE INVENTION

This disclosure relates to implantable medical devices and more particularly to implantable cardiac pacemakers used to treat ventricular dysynchrony.

BACKGROUND OF THE INVENTION

Heart failure affects approximately 5 million people in the United States. Many moderate to severe heart failure patients may also have a condition in which the two lower chambers of the heart (known as the left and right ventricles) are not beating together as they do normally. In medical terms, this condition is called "ventricular dysynchrony." Ventricular dysynchrony disturbs the synchronous beating of the heart, and as a result the heart does not pump blood adequately to meet the needs of the body. More specifically, ventricular dysynchrony typically results from intraventricular conduction delays (IVCD) that disturb the synchronous beating of the ventricles. Typically, the IVCD has a left bundle branch block (LBBB) morphology.

One previous method for optimizing cardiac pacing for intra-left ventricular resynchronization involves modifying pacing to reduce QRS duration. Even though QRS duration can be reduced, reduction in QRS duration does not guarantee optimal hemodynamic cardiac operation. Kass et al., *Improved left ventricular mechanics from acute VDD pacing in patients with dilated cardiomyopathy and ventricular conduction delay*, Circulation 1999; 99:1567–73.

Another previous method for optimizing cardiac pacing for intra-left ventricular resynchronization involves modifying pacing to improve cardiac ventricle filling. Typically cardiac ventricle filling is measured by echocardiography. Although cardiac filling is one aspect of hemodynamics, tests have shown that optimal hemodynamic cardiac operation by pacing does not result from better cardiac filling. Auricchio et al., *Cardiac resynchronization therapy restores optimal atrioventricular mechanical timing in heart failure patients with ventricular conduction delay*, J. Am Coll Cardiol 2002; 39:1163–9.

One therapy to treat left ventricle dysynchrony is Cardiac Resynchronization Therapy (CRT). CRT is a new, proven treatment for selected patients with heart failure-induced conduction disturbances and ventricular dysynchrony. When used in combination with stable, optimal medical therapy, CRT is designed to reduce symptoms by restoring the mechanical sequence of ventricular activation. Cardiac resynchronization therapy (CRT) provides atrial-synchronized, biventricular pacing using standard pacing technology combined with a special third lead which is implanted via the coronary sinus and positioned in a cardiac vein to sense and pace the left ventricle. Following a sensed atrial contraction, both ventricles are stimulated to contract more synchronous. The resulting resynchronization of ventricular contraction reduces mitral regurgitation and optimizes left ventricular filling, thereby improving cardiac function.

BRIEF SUMMARY OF THE INVENTION

Cardiac pacing for optimal intra-left ventricular resynchronization is performed as follows. Early paced inter-ventricular asynchrony is determined during ventricular pacing. Baseline inter-ventricular asynchrony is determined without pacing. Average inter-ventricular asynchrony is calculated by averaging the early paced inter-ventricular asynchrony and the baseline inter-ventricular asynchrony. Atrio-ventricular delay and ventricular-ventricular delay are adjusted during ventricular pacing to yield the average inter-ventricular asynchrony for optimal intra-left ventricular resynchronization. The elements above can be configured in software contained in an implantable medical device or embodied as a computer software product that includes a medium readable by a processor.

DETAILED DESCRIPTION OF THE INVENTION

Figure 1:
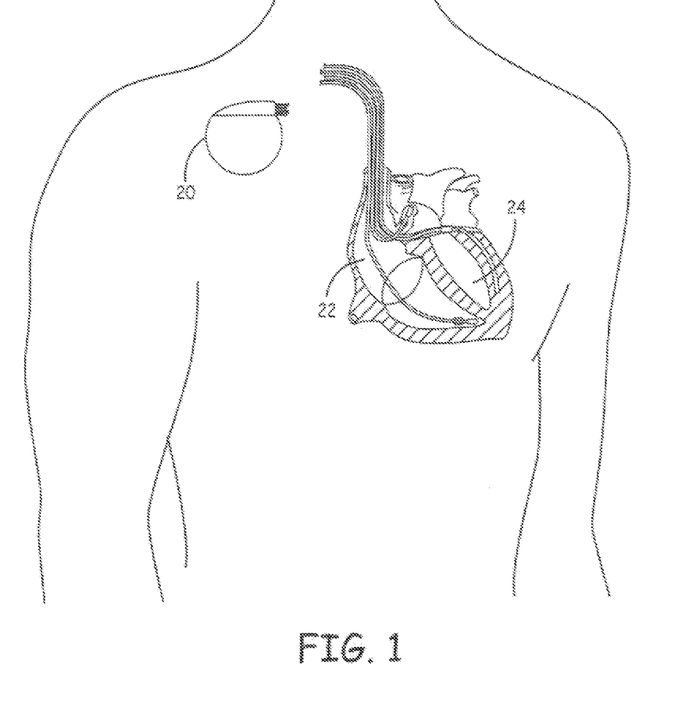
FIG. 1 shows an environmental view of an implantable cardiac device (ICD).
Figure 2:
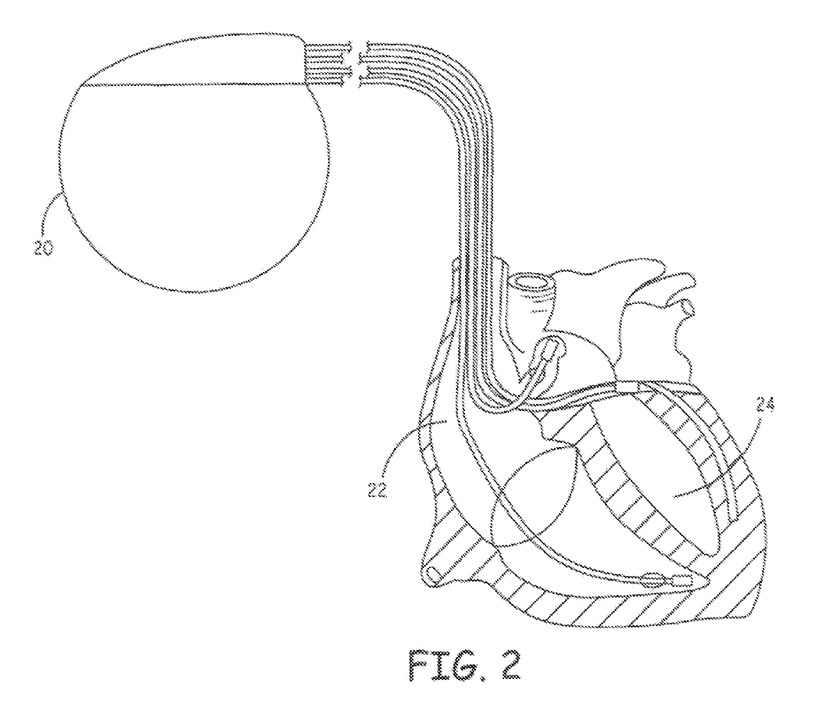
FIG. 2 shows a more detailed environmental view of an ICD.

FIGS. 1 and 2 show an environmental view of an Implantable Cardiac Device (ICD) for optimal intra-left ventricular resynchronization. The ICD can be any ICD capable pacing both the right ventricle and the left ventricle known as bi-ventricular pacing. Implantable Cardiac Devices suitable for bi-ventricular pacing include certain pacemakers, cardioverters, and defibrillators configured for bi-ventricular pacing. For example, the ICD and be an InSync® III Model 8040 pacemaker or an InSync® Marquis cardioverter/ defibrillator using two standard right heart electrical leads (in the right atrium and right ventricle) and one left-heart electrical lead such as an Attain™ Model 2187, 2188 or 4193 also available from Medtronic, Inc. in Minneapolis, Minn. USA. The left heart electrical lead is typically implanted transvenously via the coronary sinus and positioned in a cardiac vein to pace the left ventricle.

Figure 3:
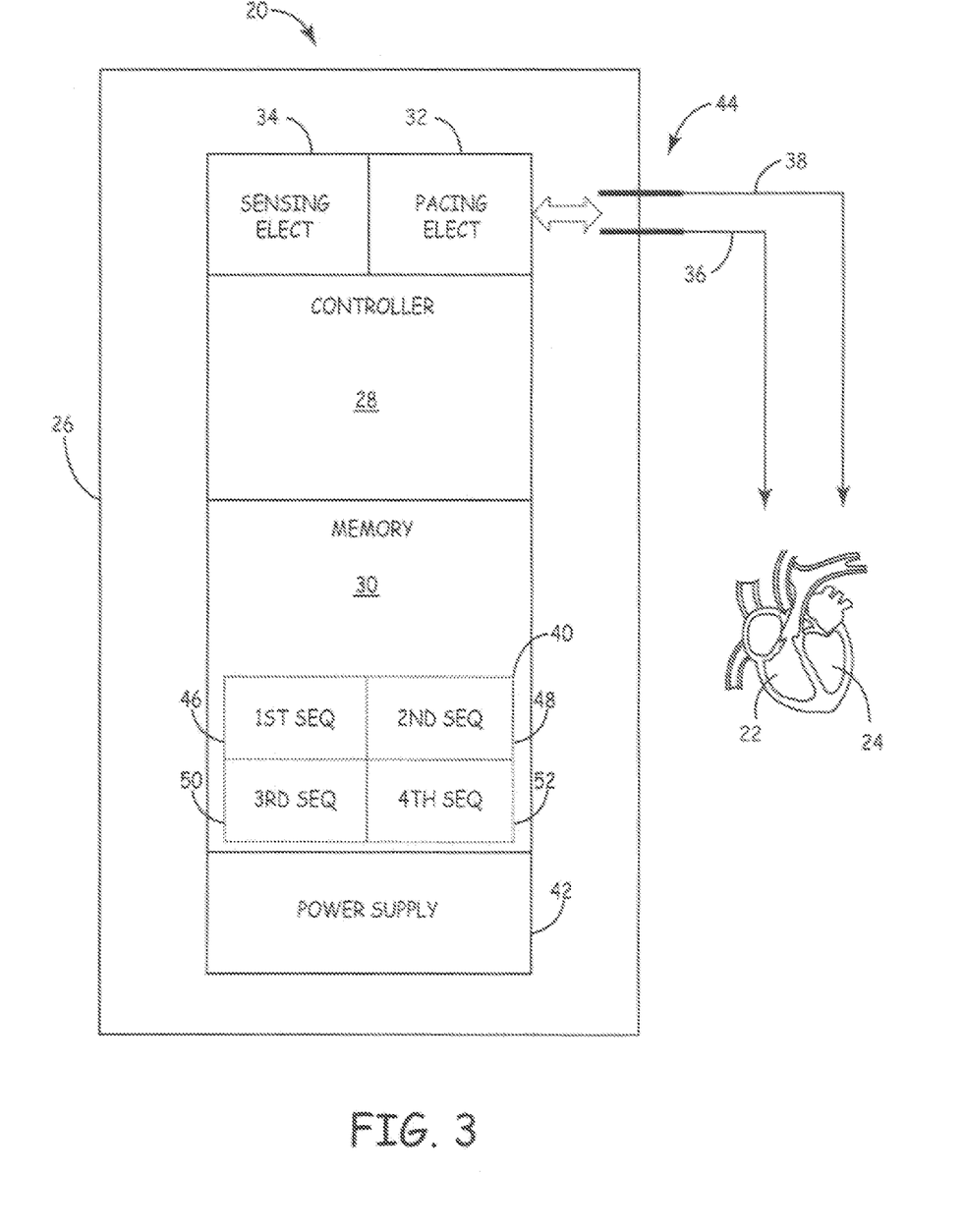
FIG. 3 shows a simplified block diagram of an ICD.

FIG. 3 shows a block diagram of an implantable cardiac device 20 for optimal intra-left ventricular resynchronization. The cardiac pacemaker 20 comprises a housing 26, a controller 28, memory 30, pacing electronics 32, sensing electronics 34, a first electrical lead 36, a second electrical lead 38, and software 40. The housing 26 has a power supply 42 carried in the housing 26 and a feedthrough 44. The controller 28 is carried in the housing 26 and coupled to the power supply 42. Memory 30 is coupled to the controller 28. The pacing electronics 32 are coupled to the controller 28 and the feedthrough 44. The sensing electronics 34 are coupled to the controller 28 and the feedthrough 44.

The first electrical lead 36 is coupled to the feedthrough 44 and configured for positioning in the right ventricle 22. The first electrical lead 36 has at least a first electrode for pacing the right ventricle 22, and the first electrical lead 36 can also have additional electrodes for functions such as pacing the right atrium. The first electrode can also serve as a sensing electrode to provide sensing signals of right ventricle 22 timing to the sensing electronics 34.

The second electrical lead 38 is coupled to the feedthrough 44 and configured for positioning in the left ventricle 24. The second electrical lead 38 has at least a second electrode for pacing the left ventricle 24, and the second electrical lead 38 can also have additional electrodes for functions such as pacing the left atrium. The second electrode can also serve as a sensing electrode to provide sensing signals of left ventrical 24 timing to the sensing electronics 34.

In addition to sensors placed on the first electrical lead 36 and second electrical lead 38, a variety of other electrical or mechanical sensors can be used to sense asynchronies such as a vectorcardiogram, bodysurface mapping, echocardiography, heartsounds, tissue Doppler Imaging, and the like.

Software 40 is stored in memory 30 that contains a first sequence of instructions 46, a second sequence of instructions 48, a third sequence of instructions 50, and a fourth sequence of instructions 52. The software 40 can be configured in the implantable medical device 20 or embodied as a computer software product that includes a medium readable by a processor. The first sequence of instructions 46 when executed by the controller 28, causes the controller 28 to receive early paced inter-ventricular asynchrony data during ventricular pacing through the first electrical lead 36 and sensing electronics 34. The first sequence of instructions 46 serves as a means for determining paced inter-ventricular asynchrony during ventricular pacing. The second sequence of instruction 48 when executed by the controller 28, causes the controller 28 to receive baseline inter-ventricular asynchrony without pacing data through the first electrical lead 36, the second electrical lead 38, and sensing electronics 34. The second sequence of instructions 48 serves as a means for determining baseline inter-ventricular asynchrony without pacing. The third sequence of instruction 50 when executed by the controller 28, causes the controller 28 to calculate average inter-ventricular asynchrony by averaging the early paced inter-ventricular asynchrony data and the baseline inter-ventricular asynchrony data. The third sequence of instructions 50 serves as a means for calculating average inter-ventricular asynchrony by averaging the paced inter-ventricular asynchrony and the baseline inter-ventricular asynchrony. The forth sequence of instructions 52 when executed by the controller 28, causes the controller 28 to adjust atrio-ventricular delay and ventricular-ventricular delay during ventricular pacing to yield the average inter-ventricular asynchrony for optimal intra-left ventricular resynchronization. The forth sequence of instructions 52 serves as a means for adjusting atrio-ventricular delay and ventricle-ventricle delay during ventricular pacing to yield the average inter-ventricular asynchrony for optimal intra-left ventricular resynchronization.

Figure 4:
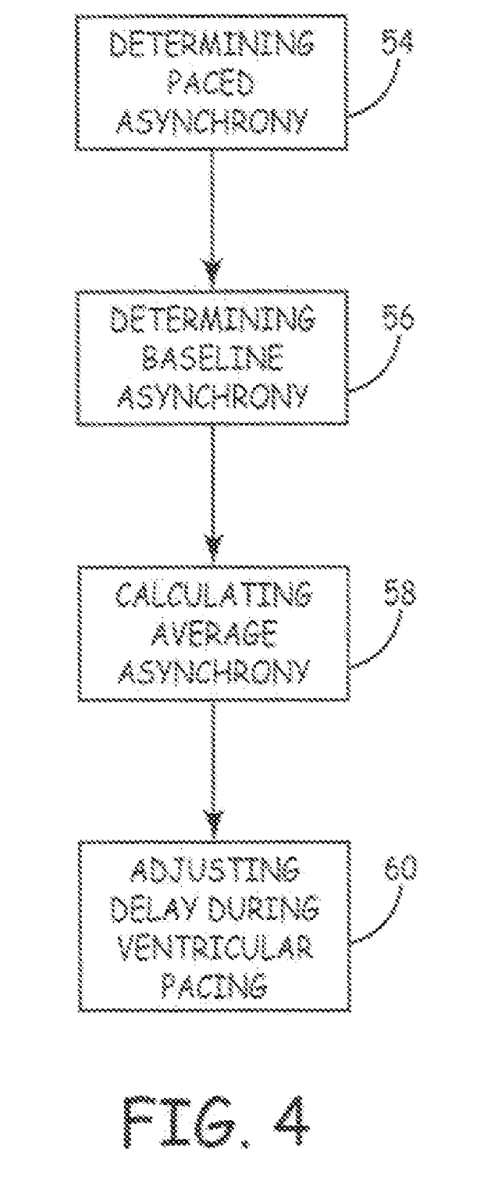
FIG. 4 shows a flowchart of a method for cardiac pacing for optimal intra-left ventricular resynchronization.

FIG. 4 shows a flowchart of a method for cardiac pacing for optimal intra-left ventricular resynchronization. The implantable cardiac device 20 such as a pacemaker operates by performing a method for optimal intra-left ventricular resynchronization that comprises the elements of determining early paced inter-ventricular asynchrony 54, determining baseline inter-ventricular asynchrony 56, calculating average inter-ventricular asynchrony 58, and adjusting delay during ventricular pacing 60. The implantable cardiac device 20 can perform intra-left ventricular resynchronization optimization automatically or through the control of a clinician. The early paced inter-ventricular asynchrony is determined 54 during ventricular pacing. The early paced inter-ventricular asynchrony is determined 54 by applying the short atrio-ventricular delay and then measuring the activation delay between the left-ventricle 22 and the right-ventricle 24. The short atrio-ventricular delay is less than 50 ms. The baseline inter-ventricular asynchrony is determined 56 without pacing. The baseline inter-ventricular asynchrony is determined 56 by measuring the activation delay between the right-ventricle 22 and the left-ventricle 24. The average inter-ventricular asynchrony is calculated 58 by averaging the early paced inter-ventricular asynchrony 54 and the baseline inter-ventricular asynchrony 56. The average inter-ventricular asynchrony 58 optimizes cardiac function by minimizing intra-left ventricular asynchrony.

Figure 5:
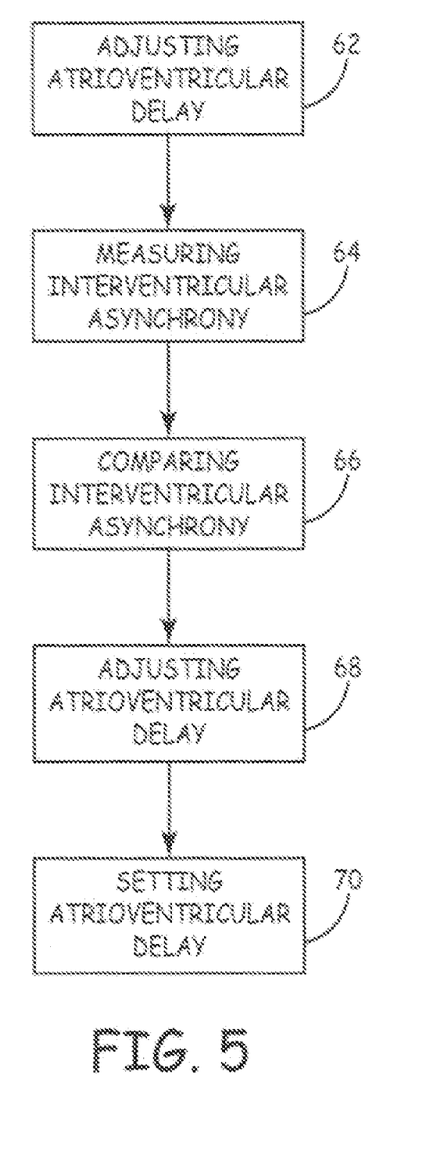
FIG. 5 shows a flowchart of a method for adjusting atrio-ventricular delay and ventricular-ventricular delay.

FIG. 5 shows a flowchart of a method for adjusting atrio-ventricular delay and ventricular-ventricular delay. The atrio-ventricular delay and ventricular-ventricular delay are adjusted during ventricular pacing to yield the average inter-ventricular asynchrony for optimal intra-left ventricular resynchronization. The atrio-ventricular delay and ventricular-ventricular delay are adjusted by adjusting atrio-ventricular delay 62, measuring the inter-ventricular asynchrony 64, comparing the inter-ventricular asynchrony 66, adjusting atrio-ventricular delay 68, and setting the atrio-ventricular delay 70. The atrio-ventricular delay 62 is adjusted by an atrio-ventricular delay increment. The ventricular-ventricular delay can be increased or decreased by a ventricular-ventricular delay increment. The inter-ventricular asynchrony is measured 64 using a sensor such as a left-ventricular pacing lead and a right-ventricular pacing lead. The inter-ventricular asynchrony is compared 66 to the average inter-ventricular asynchrony. The inter-ventricular asynchrony is compared 66 to the average inter-ventricular asynchrony by minimizing the absolute difference between the inter-ventricular asynchrony and the average inter-ventricular asynchrony. The atrio-ventricular delay is adjusted 68 by an atrio-ventricular delay increment and increasing ventricular-ventricular delay by a ventricular-ventricular delay increment. The atrio-ventricular delay increment and the ventricular-ventricular delay increment are typically less than about 30 ms. The atrio-ventricular delay and ventricular-ventricular delay is set once the average inter-ventricular asynchrony is reached.

Figure 6:
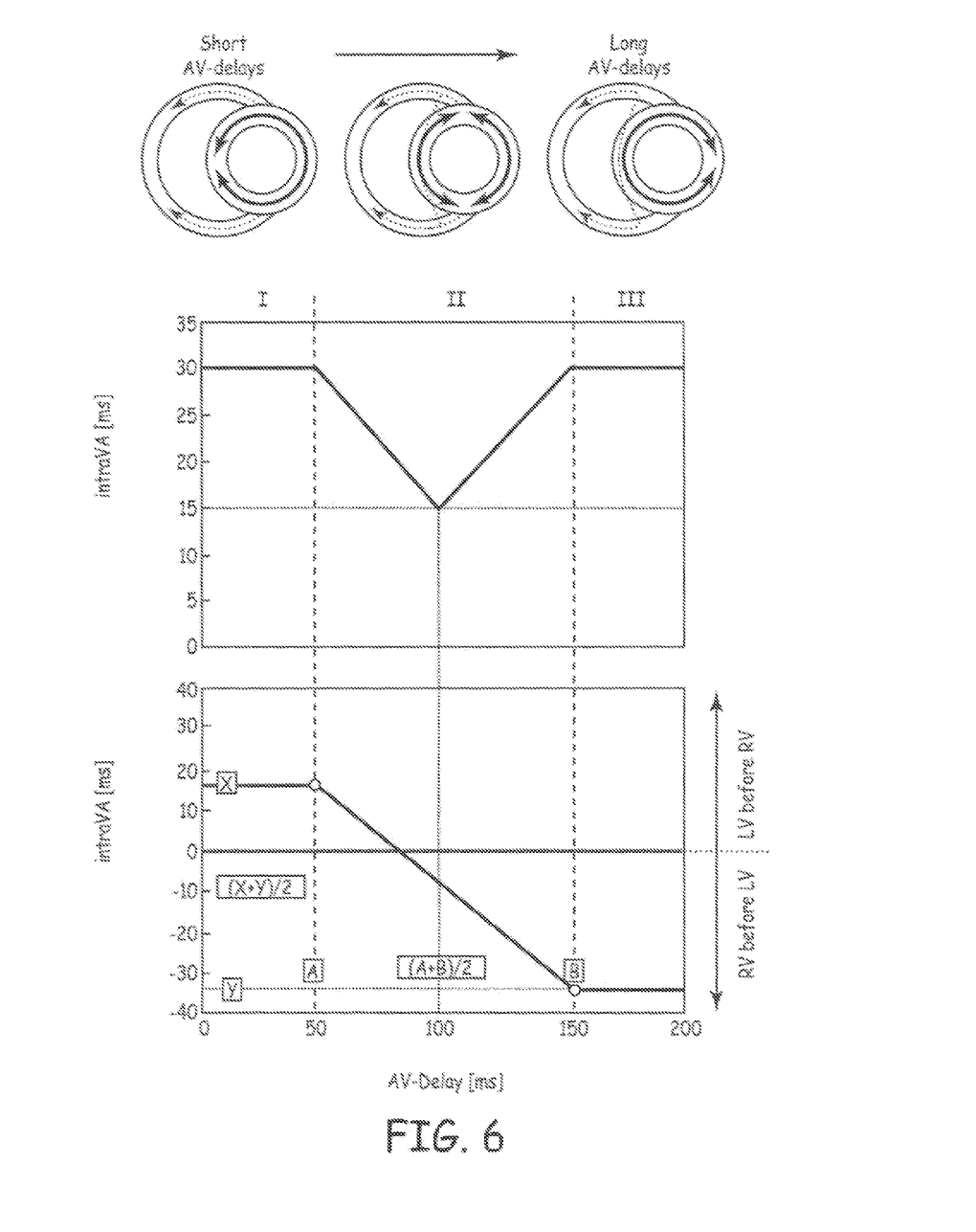
FIG. 6 shows a chart relating atrio-ventricular delay, intra-ventricular asynchrony, and inter-ventricular asynchrony during left ventricular pacing.

FIG. 6 shows a chart relating atrio-ventricular delay, intra-ventricular asynchrony, and inter-ventricular asynchrony during left ventricular pacing. The upper panel shows intrinsic (also known as endogenous) left ventricle (LV) pacing induced impulse propagation during left bundle branch block (LBBB,+LV pacing. The middle and lower panel show the relation between paced AV-delay and intraventricular asynchrony and inter-ventricular asynchrony during LBBB+LV pacing.

Table 1 data was used to develop the relationships shown above in FIG. 6. Table 1 below shows hemodynamic and asynchrony parameters before and after creation of LBBB and during LBBB+LV pacing for all experiments. Table 1 shows LBBB significantly decreased $LVdP/dt|_{max}$ and SW while intraVA and interVA significantly increased. During LBBB+optimal LV pacing $LVdP/dt|_{max}$ and SW restored when pacing with an AV-delay equal to the baseline PQ-time. At the optimum hemodynamic response, intraVA was restored to pre-LBBB values while a significant residual interVA remained present.

TABLE 1

Hemodynamic and Asynchrony Parameters

| | pre-LBBB | post-LBBB | LBBB + LVP |
|---|---|---|---|
| $LVdP/dt|_{max}$[mmHg/s] | 1627 ± 644 | 1345 ± 413* | 1929 ± 815† |
| SW [ml] | 3480 ± 1062 | 1972 ± 635* | 3224 ± 950† |
| interVA [ms] | −6 ± 9 | −28 ± 9* | −18 ± 10*† |
| intraVA [ms] | 5 ± 2 | 18 ± 3* | 4 ± 2† |
| PQ-time$|_{LBBB}$-AV-delay [ms] | — | — | 1 ± 6 |

*,† vs. pre and post LBBB resp. (P < 0.05)

In FIG. 6, the data graphed is from one animal experiment with the solid lines showing the following conceptual relationship. I: LBBB+LV pacing at short AV-delays; the ventricles are completely activated by pacing induced activation resulting in a fixed degree of intraVA and interVA (X). II: LBBB (or LBBB+LV pacing with long AV-delays); endogenous activation entirely determines ventricular activation resulting in a fixed degree of intraVA and interVA (Y). III: LBBB+LV pacing at intermediate AV-delays (ranging from A and B); fusion between pacing induced and endogenous activation. Minimal intraVA occurs when pacing induced and endogenous activation meet halfway. This results in a residual degree of interventricular asynchrony equal to (X+Y)/2 which occurs at an AV-delay equal to (A+B)/2.

Based on the results from animal experiments on asynchrony during pacing, a model for the behavior of asynchrony as a function of the timing of pacing was developed. With this model, the degree of residual inter-ventricular asynchrony at the optimal cardiac pump function can be predicted. This allows for optimization of pacing therapy based on measurements of inter- instead of intra-ventricular asynchrony. An advantage of this approach is that measures for inter-ventricular asynchrony are relatively simple compared to the complex techniques required for accurate intra-ventricular asynchrony measurements. Inter-ventricular asynchrony can be assessed by non-invasive measures such as the timing differences in opening of aortic and pulmonary valves by echocardiography, Tissue Doppler, heart sound, and the like. Unfortunately, MRI technology is not suitable for most pacemaker patients.

Figure 7:
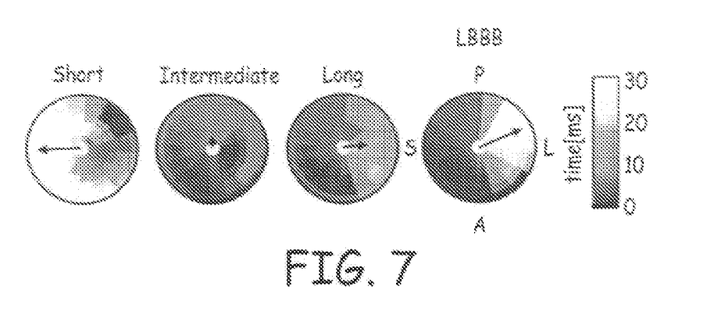
FIG. 7 shows bulls-eye plots of left-ventricular (LV) endocardial activation times during left bundle branch block (LBBB)+LV later wall pacing.

FIG. 7 shows bulls-eye plots of left-ventricular (LV) endocardial activation times during left bundle branch block (LBBB)+LV lateral wall pacing with short, intermediate and long AV-delays and during baseline in one animal. The inner radius of the bulls-eye plots represents the LV apex and the outer radius the LV base. Location of the Septum, Anterior, Lateral and Posterior wall is indicated by S, A, L and P respectively in the baseline LBBB plot. The arrows in the plots represent the Activation Delay Vectors (ADV), which is the directional sum of activation times. The amplitude of the ADV is a measure for the degree of interVA and the angle of the ADV represents the main direction of conduction.

Figure 8:
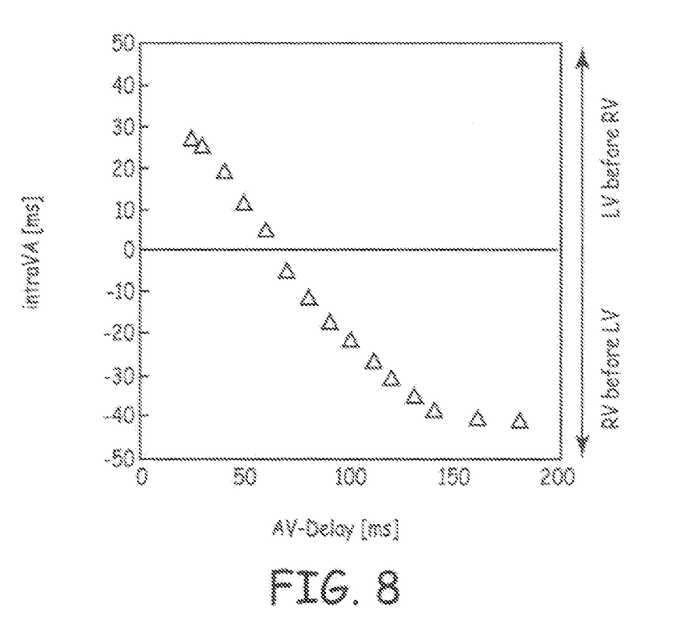
FIG. 8 shows a graph of inter-ventricular asynchrony (interVA) as a function of the atrio-ventricular delay (AV-delay) during left bundle branch block (LBBB)+left ventricle (LV) pacing.

FIG. 8 shows a graph of inter-ventricular asynchrony (interVA) as a function of the atrio-ventricular delay (AV-delay) during left bundle branch block (LBBB)+left ventricle (LV) pacing.

Figure 9:
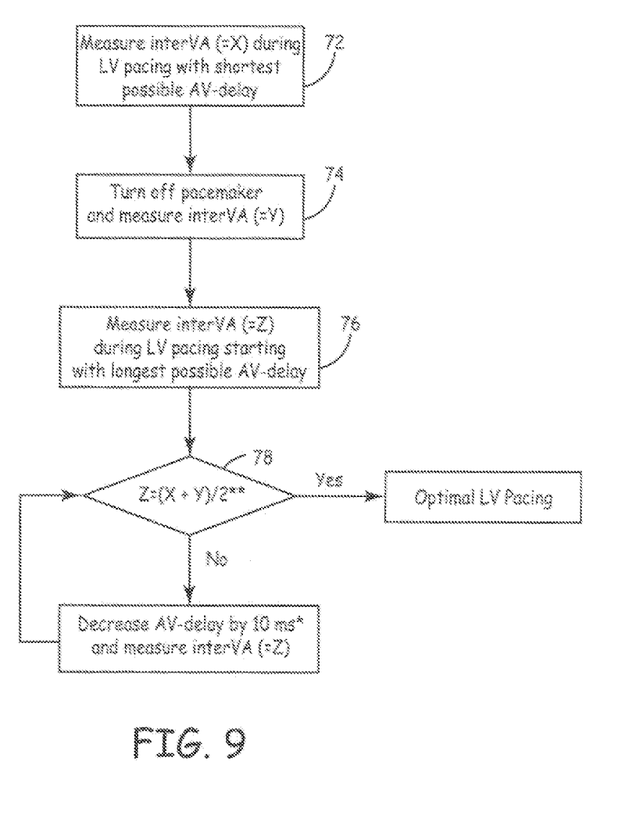
FIG. 9 shows a flowchart of optimization of interventricular asynchrony (interVA) for maximal hemodynamic effect during left-ventricle (LV) pacing.

FIG. 9 shows a flowchart of optimization of interventricular asynchrony for maximal hemodynamic effect during left-ventricle (LV) pacing. The degree of interventricular asynchrony is measured 72 during LV pacing with a short AV-delay and measured 74 during the unpaced situation resulting in interVAs of X and Y, respectively. Then, starting with pacing with the longest possible AV-delays, the AV-delays is gradually decreased while measuring interventricular asynchrony (Z) 76. Once Z equals (X+Y)/2 78 pacing is optimal. The time of 10 ms is an arbitrary value. To account for noise/errors in interventricular asynchrony during the decision calculation (X, Y and Z), this may be replaced by minimization of the absolute difference between Z and (X+Y)/2. If the minimum is reached, LV pacing is optimal.

Figure 10:
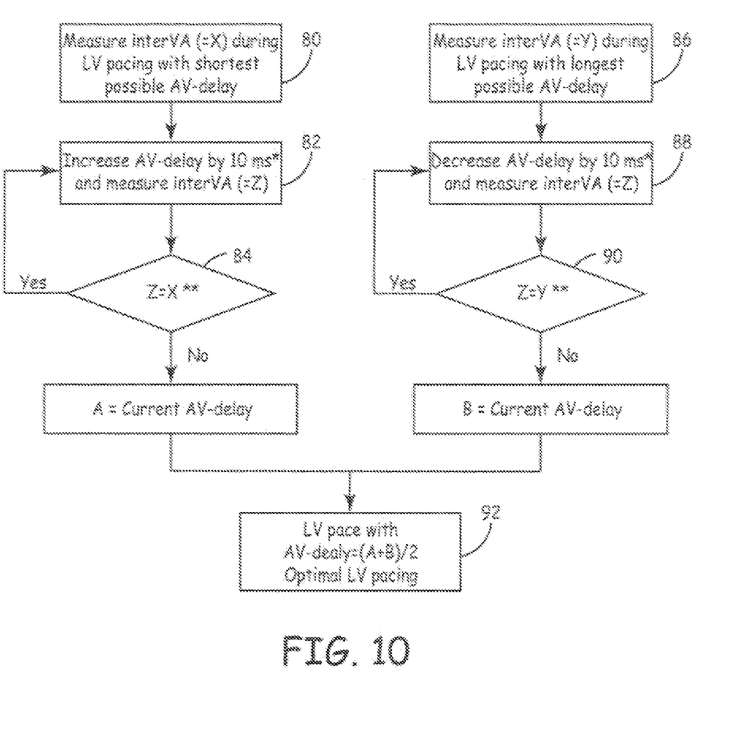
FIG. 10 shows a flowchart of an alternative approach to maximize hemodynamic effect of left-ventricular (LV) pacing.

FIG. 10 shows a flowchart of an alternative approach to maximize hemodynamic effect of left-ventricular (LV) pacing by optimization of the AV-delay via interventricular asynchrony measurements. During pacing with the shortest possible AV-delay, interVA is measured (X) 80. Next, the AV-delay is stepwise increased while measuring interVA (Z) 82. Increasing the AV-delay continues until Z no longer equals X (AV-delay=A) 84. Similarly, during pacing with the longest possible AV-delay interVA is measured (Y) 86. Next, the AV-delay is stepwise decreased while measuring interVA (Z) 88. Decreasing the AV-delay continues until Z no longer equals Y (AV-delay=B) 90. The optimal AV-delay for LV-pacing equals (A+B)/2 92. The time of 10 ms is an arbitrary value. To account for noise/errors in interventricular asynchrony during the decision calculation (X, Y and Z), the decision calculation can be replaced by the comparison (Z−X)<5 ms and (Z−Y)<5 ms (5 ms value arbitrary).

Figure 11:
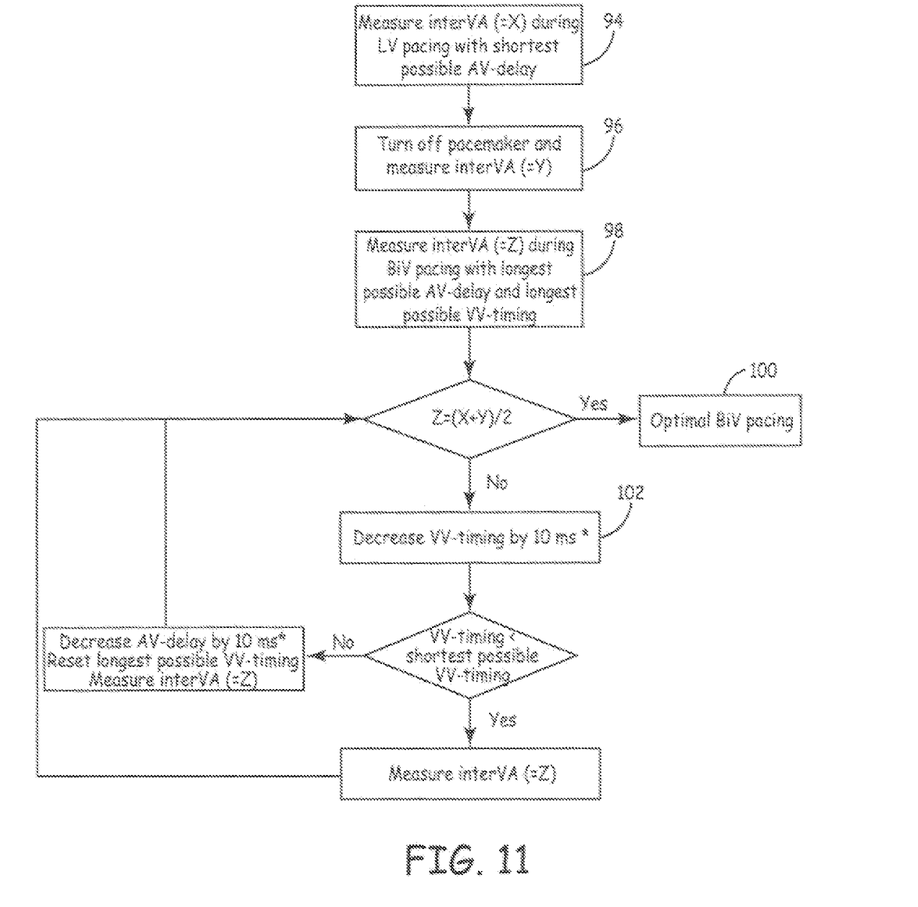
FIG. 11 shows a flowchart of optimization of interventricular asynchrony (interVA) for maximal hemodynamic effect during bi-ventricular (BiV) pacing.

FIG. 11 shows a flowchart of optimization of interventricular asynchrony for maximal hemodynamic effect during bi-ventricular (Bi-V) pacing. The degree of interventricular asynchrony is measured during LV pacing with a short AV-delay 94 and during the unpaced situation 96 resulting in interVAs of X and Y, respectively. Interventricular asynchrony is measured (Z) 98 with BiV pacing having the longest possible AV-delays (e.g. 200 ms) and the longest possible VV-timing (e.g. +50 ms). VV-timing is stepwise decreased until the shortest possible VV-timing is achieved (e.g. −50 ms) while interVA is measured (Z). Once the degree of interventricular asynchrony (Z) equals (X+Y)/2 pacing is optimal 100. If this does not occur for all tested VV-timing the process is repeated but now during BiV pacing with an AV-delay that is decreased by 10 ms 102. In this approach all combinations of AV-delay and VV-timing are tested. However, it is likely that the condition Z=(X+Y)/2 is fulfilled at more than one combination of VV-timing and AV-delay. Therefore, instead of starting with the longest possible AV-delay, an arbitrary choice may be made for the AV-delay to begin with. The time of 10 ms is an arbitrary value. To account for noise/errors in interventricular asynchrony (X, Y and Z) this may be replaced by minimization of the absolute difference between Z and (X+Y)/2. If the minimum is reached, LV pacing is optimal.

Table 2 below shows a list of symbols that will be used in equations to show theoretical background to cardiac pacing for optimal intra-left ventricular resynchronization.

TABLE 2

List of Symbols

| Symbol | Definition |
|---|---|
| interVA | interventricular asynchrony [ms] {variable} |
| interVA$\|_{opt}$ | predicted degree of interventricular asynchrony [ms] at optimal LV function {constant} |
| interVA$\|_{BL}$ | interventricular asynchrony during baseline [ms] (no pacing) {constant} |
| interVA$\|_{LVP}$ | interventricular asynchrony during LV pacing [ms] {variable} |
| interVA$\|_{RVP}$ | interventricular asynchrony during RV pacing [ms] {variable} |
| interVA$\|_{BiVP}$ | interventricular asynchrony during BiV pacing [ms] {variable} |
| VV | VV-timing [ms] {variable} |
| AVD | AV-delay [ms] {variable} |
| AVD$\|_{LV}$ | AV-delay of the LV [ms] {variable} |
| AVD$\|_{RV}$ | AV-delay of the RV [ms] {variable} |
| AVD0 | shortest possible AV-delay [ms] {constant} |
| LVF | LV pump function (e.g. LVdP/dt$\|_{max}$, LV Stroke Work or Aortic Pulse Pressure) {variable} |

Prediction of optimal inter-VA during LV and BiV pacing. Based on the conceptual relation between AV-delay and ventricular asynchrony the following equation can be derived to predict the degree of interVA at optimal hemodynamic response during LV pacing;

$$\text{interVA}|_{opt} = \frac{1}{2} \cdot [\text{interVA}(AVD0)|_{LVP} + \text{interVA}|_{BL}] \quad \text{Equation 1}$$

with AVD0, the shortest possible AV-delay, interVA(AVD0)$\|_{LVP}$ the degree of interVA during LV pacing at AVD0 and interVA$\|_{BL}$, the degree of interVA during baseline (unpaced LBBB). The same optimal degree of interVA is also valid during BiV pacing since, animal experiments showed that at similar degrees of interVA, LV and BiV pacing produced an equal hemodynamic response;

$$LVF(\text{interVA})|_{BiVP} = LVF (\text{interV})|_{LVP} \quad \text{Equation 2}$$

with LVF, LV function during LV pacing (LVP) and BiV pacing (BiVP). Consequently, the same interVA$\|_{opt}$ is valid for BiV pacing.

Figure 12:
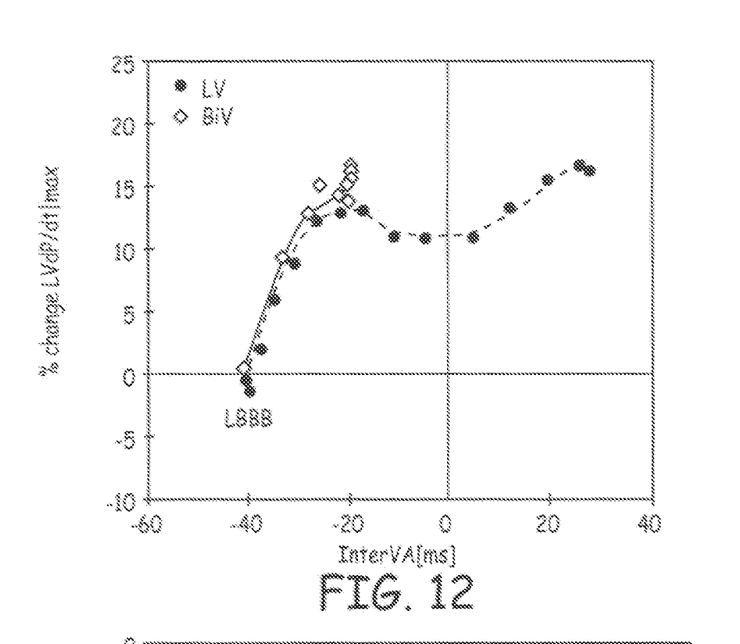
FIG. 12 shows a graph of the relative change in LVdP/dt|max in percent during left ventricle (LV) and bi-ventricle (BiV) pacing in a canine heart with left bundle branch block (LBBB).

FIG. 12 shows a graph of the relative change in LVdP/dt$\|$max in percent during left ventricle (LV) and bi-ventricle (BiV) pacing in a canine heart with left bundle branch block (LBBB). The graph shows typical examples of the hemodynamic response as a function of interVA in one animal experiment and in a patient during LV and BiV pacing. This graph illustrates that the hemodynamic response during BiV pacing equals the hemodynamic response during LV pacing at equal interVA. During BiV pacing however, the degree of interVA that could be achieved was smaller than during LV pacing.

Effect of AV-delay and VV-timing on interVA during BiV pacing. During BiV pacing the degree of interVA at each AV-delay, was equal to the average of the degree of interVA during LV pacing alone and the degree of interVA during RV pacing alone at the same AV-delay. Thus;

$$\text{interVA}(AVD)|_{BiVP} = \frac{1}{2} \cdot [\text{interVA}(AVD)|_{LVP} + \text{interVA}(AVD)|_{RVP}] \quad \text{Equation 4}$$

with AVD, the AV-delay.

Figure 13:
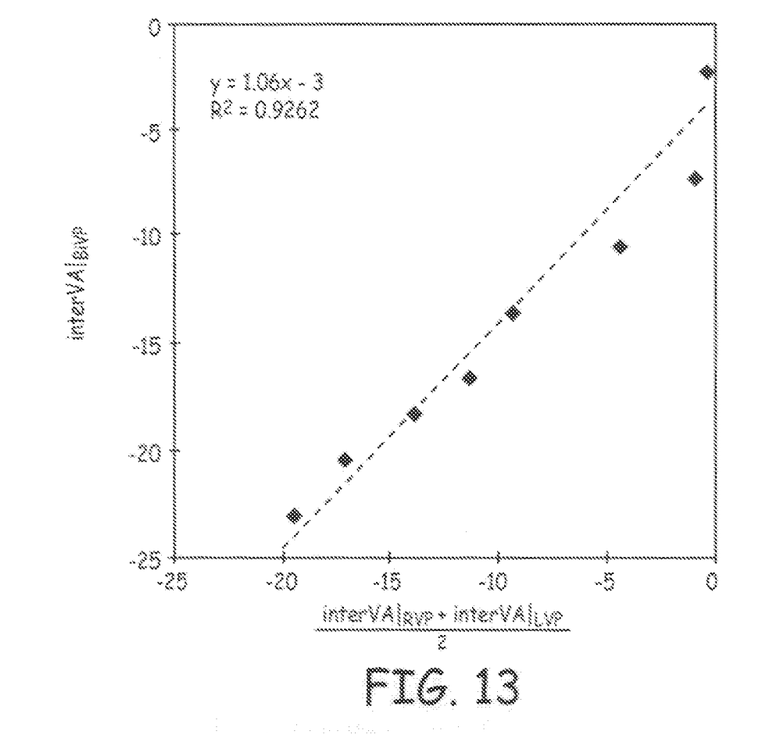
FIG. 13 shows a graph of inter-ventricular asynchrony (interVA) during bi-ventricular (BiV) pacing versus the average interVA during left ventricle (LV) and right ventricle (RV) pacing for all atrio-ventricular delays (AV-delays).

FIG. 13 shows a graph of inter-ventricular asynchrony (interVA) during bi-ventricular (BiV) pacing versus the average interVA during left ventricle (LV) and right ventricle (RV) pacing for all atrio-ventricular delays (AV-delays). This graph shows a typical example of interVA during BiV pacing versus the average degree of interVA during LV and RV pacing. Linear regression resulted in a near unity slope and only a small intercept of 3 ms.

To extend the application to different VV-timing which can be applied during BiV pacing it should be noted that;

$$VV = AVD|_{RV} - AVD|_{LV} \quad \text{Equation 4}$$

with AVD$\|_{RV}$ and AVD$\|_{LV}$ the AV-delays of the RV and LV respectively. By definition VV>0 if the LV is activated prior to the RV. Based on Equation 3 and Equation 4 we postulate;

$$\text{interVA}(VV)|_{BiVP} = \frac{1}{2} \cdot [\text{interVA}(AVD|_{LV})|_{LVP} + \text{interVA}(AVD|_{RV})|_{RVP}] \quad \text{Equation 5}$$

Because pacemakers don't differentiate between LV and RV AV-delays it should be noted that if $VV>0$ $AVD|_{LV} = AVD$ $AVD|_{RV} = AVD + VV$ if $VV<0$ $AVD|_{LV} = AVD - VV$ $AVD|_{RV} = AVD \quad \text{Equation 6}$ In this case Equation 5 changes to if $VV>0$ $\text{interVA}(VV,AVD)|_{BiVP} = \frac{1}{2} \cdot [\text{interVA}(AVD)|_{LVP} + \text{interVA}(AVD+VV)|_{RVP}]$ if $VV<0$ $\text{interVA}(VV,AVD)|_{BiVP} = \frac{1}{2} \cdot [\text{interVA}(AVD-VV)|_{LVP} + \text{interVA}(AVD)|_{RVP}]$ Equation 7

Figure 14:
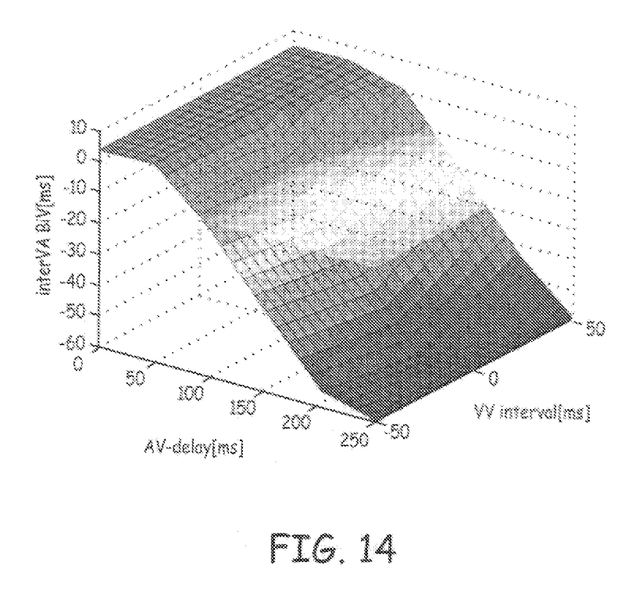
FIG. 14 shows three dimensional graph of the relationship between interventricular asynchrony (interVA) during bi-ventricular (BiV) pacing as a function of atrio-ventricular delay (AV-delay) and ventricular ventricular interval (VV-interval).

FIG. 14 shows three-dimensional graph of the relationship between interVA during BiV pacing as a function of AV-delay (x-axis) and VV-interval (y-axis). The colors in the 3 D-plane represent the level of interVA during BiV pacing, which is also displayed on the z-axis. In this example characteristic parameters of the heart were set to user defined values (interVA(AVD0)$\|_{LVP}$, interVA(AVD0)$\|_{RVP}$ and interVA$\|_{BL}$). The transparent 2 D-plane represents a constant interVA value at which BiV pacing is optimal. Cross section of this plane with the colored 3 D-plane represents the combination of AV-delays and VV-interval at which BiV pacing is optimal. FIG. 14 was constructed based on the above equations and knowledge of a few characteristic asynchrony parameters of the heart (interVA(AVD0)$\|_{LVP}$, interVA(AVD0)$\|_{RVP}$ and interVA$\|_{BL}$) which were user defined in this example. The transparent plane in this figure represents the degree of interVA$\|_{opt}$ at optimal hemodynamic response. The intercept with this transparent plane represents all combinations of the AV-delay and VV-timing leading to an optimal hemodynamic response.

Thus, embodiments of the cardiac pacing for optimal intra-left ventricular resynchronization are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of cardiac pacing for optimal intra-left ventricular resynchronization, comprising:
   determining an early paced inter-ventricular asynchrony during ventricular pacing;

determining a baseline inter-ventricular asynchrony without pacing;

calculating an average inter-ventricular asynchrony by averaging the early paced inter-ventricular asynchrony and the baseline inter-ventricular asynchrony; and, adjusting atrio-ventricular delay and ventricular-ventricular delay during ventricular pacing to yield the average inter-ventricular asynchrony for intra-left ventricular resynchronization.

2. The method as in claim 1, wherein the average inter-ventricular asynchrony optimizes cardiac function by minimizing intra-left ventricular asynchrony.

3. The method as in claim 1, wherein the early paced inter-ventricular asynchrony is determined by applying a short atrio-ventricular delay and then measuring an activation delay between the left-ventricle and the right-ventricle.

4. The method as in claim 3, wherein the short atrio-ventricular delay is less than 50 ms.

5. The method as in claim 1, wherein the baseline inter-ventricular asynchrony is determined by measuring an activation delay between a left-ventricle and a right-ventricle.

6. The method as in claim 1, wherein intra-left ventricular resynchronization is optimized automatically by the implantable cardiac device.

7. The method as in claim 1, wherein paced inter-ventricular asynchrony is determined during ventricular pacing using left ventricular pacing with a short atrio-ventricular delay.

8. The method as in claim 1, wherein atrio-ventricular delay and ventricular-ventricular delay are adjusted by adjusting atrio-ventricular delay by an atrio-ventricular delay increment and increasing ventricular-ventricular delay by a ventricular-ventricular delay increment, measuring an inter-ventricular asynchrony, comparing the inter-ventricular asynchrony to the average inter-ventricular asynchrony, adjusting atrio-ventricular delay by an atrio-ventricular delay increment and increasing or decreasing ventricular-ventricular delay by a ventricular-ventricular delay increment, and, setting the atrio-ventricular delay and ventricular-ventricular delay once the average inter-ventricular asynchrony is reached.

9. The method as in claim 8, wherein the atrio-ventricular delay increment and the ventricular-ventricular delay increment are less than about 30 ms.

10. The method as in claim 8, wherein the inter-ventricular asynchrony is sensed using a left-ventricular pacing lead and a right-ventricular pacing lead.

11. The method as in claim 8, wherein comparing the inter-ventricular asynchrony to the average inter-ventricular asynchrony is performed by minimizing the absolute difference between the inter-ventricular asynchrony and the average inter-ventricular asynchrony.

12. A cardiac pacemaker configured for optimizing intra-left ventricular resynchronization, comprising:

means for determining an early paced inter-ventricular asynchrony during ventricular pacing;

means for determining a baseline inter-ventricular asynchrony without pacing;

means for calculating average inter-ventricular asynchrony by averaging the paced inter-ventricular asynchrony and the baseline inter-ventricular asynchrony;

means for adjusting atrio-ventricular delay and ventricle-ventricle delay during ventricular pacing to yield the average inter-ventricular asynchrony for intra-left ventricular resynchronization.

13. A cardiac pacemaker for optimal intra-left ventricular resynchronization, comprising:

a housing having a power supply carried in the housing and a feedthrough;

a controller carried in the housing coupled to the power supply;

memory coupled to the controller;

pacing electronics coupled to the controller and the feedthrough;

sensing electronics coupled to the controller and the feedthrough;

a first electrical lead coupled to the feedthrough and configured for positioning in the right ventricle;

a second electrical lead coupled to the feedthrough and configured for positioning in the left ventricle;

software stored in memory containing instructions including, a first sequence of instructions when executed by the controller, causes the controller receive an early paced inter-ventricular asynchrony data during ventricular pacing through the first electrical lead and sensing electronics, a second sequence of instruction when executed by the controller, causes the controller to receive a baseline inter-ventricular asynchrony without pacing data through the first electrical lead, the second electrical lead, and sensing electronics, a third sequence of instruction when executed by the controller, causes the controller to calculate average inter-ventricular asynchrony by averaging the early paced inter-ventricular asynchrony data and the baseline inter-ventricular asynchrony data, and, a forth sequence of instruction when executed by the controller, causes the controller to adjust atrio-ventricular delay and ventricular-ventricular delay during ventricular pacing to yield the average inter-ventricular asynchrony for optimal intra-left ventricular resynchronization.

14. A cardiac pacemaker for optimal intra-left ventricular resynchronization, comprising:

a housing having a power supply carried in the housing and a feedthrough;

a controller carried in the housing coupled to the power supply;

memory coupled to the controller;

pacing electronics coupled to the controller and the feedthrough;

sensing electronics coupled to the controller and the feedthrough;

a first electrical lead coupled to the feedthrough and configured for positioning in the right ventricle;

a second electrical lead coupled to the feedthrough and configured for positioning in the left ventricle;

means for determining an early paced inter-ventricular asynchrony during ventricular pacing;

means for determining a baseline inter-ventricular asynchrony without pacing;

means for calculating average inter-ventricular asynchrony by averaging the paced inter-ventricular asynchrony and the baseline inter-ventricular asynchrony; and, means for adjusting atrio-ventricular delay and ventricle-ventricle delay during ventricular pacing to yield the average inter-ventricular asynchrony for intra-left ventricular resynchronization.

15. A computer software product that includes a medium readable by a processor, the medium having stored thereon instructions for cardiac pacing for optimal intra-left ventricular resynchronization in an implantable cardiac, comprising:
- a first sequence of instructions when executed by the controller, causes the controller receive an early paced inter-ventricular asynchrony data during ventricular pacing;
- a second sequence of instruction when executed by the controller, causes the controller to receive a baseline inter-ventricular asynchrony without pacing data;
- a third sequence of instruction when executed by the controller, causes the controller to calculate average inter-ventricular asynchrony by averaging the early paced inter-ventricular asynchrony data and the baseline inter-ventricular asynchrony data; and,
- a forth sequence of instruction when executed by the controller, causes the controller to adjust atrio-ventricular delay and ventricular-ventricular delay during ventricular pacing to yield the average inter-ventricular asynchrony for intra-left ventricular resynchronization.

* * * * *